United States Patent [19]

Ackermann et al.

[11] Patent Number: 4,468,353

[45] Date of Patent: Aug. 28, 1984

[54] METHOD OF PREPARING ALKOXYMETHYLENE COMPOUNDS

[75] Inventors: Otto Ackermann, Troisdorf Sieglar; Dieter Bretzinger, Lohmer; Herbert Schneidewind; Rudolf Stephan, both of Troisdorf, all of Fed. Rep. of Germany

[73] Assignee: Dynamit Nobel AG, Troisdorf, Fed. Rep. of Germany

[21] Appl. No.: 432,051

[22] Filed: Sep. 30, 1982

Related U.S. Application Data

[60] Continuation of Ser. No. 200,841, Oct. 27, 1980, abandoned, which is a division of Ser. No. 15,096, Feb. 26, 1979, Pat. No. 4,277,418, which is a continuation-in-part of Ser. No. 825,794, Aug. 9, 1977, abandoned.

[30] Foreign Application Priority Data

Aug. 10, 1976 [DE] Fed. Rep. of Germany ....... 2635841

[51] Int. Cl.$^3$ .................. C07C 120/00; C07C 121/30; C07C 121/453; C07C 121/413
[52] U.S. Cl. .............................. 260/465.4; 260/465.6; 560/174; 568/391; 568/413
[58] Field of Search .......................... 260/465.4, 465.6; 560/174; 568/391, 413

[56] References Cited

U.S. PATENT DOCUMENTS

| | | | |
|---|---|---|---|
| 2,306,765 | 12/1942 | Stiller | 560/174 X |
| 2,422,598 | 6/1947 | Stiller | 560/174 X |
| 2,824,121 | 2/1958 | Nicholl et al. | 260/465.6 X |
| 4,058,553 | 11/1977 | Ackermann et al. | 560/180 |
| 4,277,418 | 7/1981 | Ackermann et al. | 260/465.4 |

FOREIGN PATENT DOCUMENTS

| | | |
|---|---|---|
| 1770099 | 3/1972 | Fed. Rep. of Germany . |
| 2306201 | 8/1973 | Fed. Rep. of Germany ...... 560/174 |
| 2426964 | 12/1975 | Fed. Rep. of Germany . |

OTHER PUBLICATIONS

Fuson, et al., J. Org. Chem., 11, (1946), pp. 194–198.
Post, et al., J. Org. Chem., 2, (1937), pp. 260–266.
Claisen, Ber., 26, (1893), pp. 2729–2735.
Claisen, Ann., 297, (1897), pp. 19–20.
J.A.C.S., 82, (1960), p. 5533.
Kirk–Othmer, Encyclopedia of Chem. Tech., 2nd ed., vol. 1, pp. 214–222.
The Condensed Chemical Dictionary, 8th ed., p. 515.
Morrison & Boyd, Org. Chem., pp. 22–24, Allyn & Bacon, Inc., Boston.

*Primary Examiner*—Joseph Paul Brust
*Attorney, Agent, or Firm*—Sprung, Horn, Kramer & Woods

[57] ABSTRACT

An improvement in the alkoxylation of a compound having a reactive methylene group by contacting said compound with an orthoformic acid trialkyl ester in the presence of a catalyst, the improvement residing in employing at least 1.6 moles of orthoformic acid ester per mole of compound having a reactive methylene group and carrying out the process in the presence of a catalyst of the group of aliphatic carboxylic acids, anhydrides of aliphatic carboxylic acids, aromatic sulphonic acids, alkali metal alcoholates and alkanolamines.

6 Claims, No Drawings

METHOD OF PREPARING ALKOXYMETHYLENE COMPOUNDS

CROSS REFERENCE TO RELATED APPLICATION

This is a continuation of Ser. No. 06/200,841 filed Oct. 27, 1980, now abandoned which in turn is a divisional application of Ser. No. 015,096 filed Feb. 26, 1979 now U.S. Pat. No. 4,277,418 issued July 7, 1981 which in turn is a continuation-in-part of Ser. No. 825,794, filed Aug. 9, 1977, now abandoned.

BACKGROUND OF THE INVENTION

1. Field of the Invention

This invention relates to a process for the alkoxylation of compounds having reactive methylene groups. More especially, this invention relates to the preparation of such alkoxymethylene compounds by reaction of compounds having a reactive methylene group with excess orthoformic acid ester in the presence of a catalyst. This invention is particularly concerned with the preparation of alkoxymethylene compounds in substantially quantitative amounts where the alkoxymethylene compound is recovered in high purity.

2. Discussion of the Prior Art

L. Claisen, in "Berichte" 26, 2729 (1893), and Ann. 297, 19 (1897), described the condensation of orthoformic acid esters with compounds containing reactive methylene groups in the presence of acetic acid anhydride as catalyst. The mechanism of this reaction was thoroughly studied by Post, J. Org. Chem. 2, 260 (1937) and by Fuson, J. Org. Chem. 11, 194 to 198 (1946).

A description is furthermore given in U.S. Pat. No. 2,824,121 of the preparation of alkoxymethylene compounds from orthoformic acid triethyl esters and compounds containing reactive methylene groups, in the presence of acetic acid anhydride as catalyst. The preparation of this compound in the presence of excess orthoformic acid ester is also described in U.S. Pat. No. 4,058,553. In this method, carboxylic acids and their anhydrides as well as Lewis acids must be present as catalysts in order to obtain the desired high transformation together with good yields.

The first-named methods have the disadvantage that the reactions of the two reaction components with one another are incomplete, and numerous by-products form which considerably reduce the yield. The volatile by-products are, some of them, very difficult to separate by distillation from the alkoxymethylene compounds. The solid by-products reduce the yield and make refinement difficult. On this account the economical preparation of the pure alkoxymethylene serivatives is made difficult and in some cases impossible.

In the method U.S. Pat. No. 4,058,553, the simultaneous use of two different catalysts is disadvantageous. The amount of catalyst is accordingly relatively great.

It is an object of this invention, therefore, to provide an improved process for the production of such alkoxylated methylene compounds where the alkoxylated methylene compounds are obtained in a virtually quantitative yield. More especially, it is an object of this invention to provide an improved process for the production of such alkoxymethylene compounds which does not require a multi-component catalyst system. It is a further object of this invention to provide such alkoxymethylene compounds especially alkoxymethylene malonic acid derivatives in high yields and in high purity. These and other objects of this invention become apparent in the following description and claims.

SUMMARY OF THE INVENTION

Broadly, this invention contemplates an improvement in the process for preparing an alkoxymethylene malonic acid derivative by reaction of an orthoformic acid ester with a compound containing a reactive methylene group, the improvement comprising carrying out the process employing an excess of orthoformic acid ester and performing the process in the presence of a catalyst of the group of aliphatic carboxylic acids, anhydrides of aliphatic carboxylic acids and optionally aromatic sulfonic acids, alkali metal alcoholates and alkanolamines. Especially contemplated as catalyst is acetic anhydride.

It has been discovered in accordance with the disclosure in said Ser. No. 825,794, the disclosure of which is hereby incorporated herein by reference, that alkoxymethylene malonic acid derivatives can be prepared in virtually quantitative yields by a process which does not require multi-component catalyst system if the process is carried out employing an excess of orthoformic acid ester employing a catalyst as named above and the alcohol which forms during the process is continuously removed, e.g., by distillation.

In accordance with the invention, the alkoxymethylene malonic acid derivative is formed by reaction of the orthoformic acid ester and the malonic acid derivative having a reactive methylene group employing at least 1.6 mole of orthoformic acid ester per mole of a compound possessing a reactive methylene group. The alcohol that forms during the process is preferably removed by distillation as it forms. Preferably, the mole ratio of orthoformic acid ester to malonic acid compound containing reactive methylene group is 1.6 to 6:1. A further excess of orthoformic acid does not bring any economic advantages.

The reaction of the malonic acid derivatives put in is virtually quantitative, hardly any by-products being formed. The work-up and purification of the products obtained is quite simple.

The formation of undesired by-products is almost entirely prevented by use of excess orthoformic acid esters and by the continuous separation of the alcohol that forms. In addition to its function as a component of the reaction, the ortho ester that is present in excess suppresses the formation of by-products that might appreciably reduce the yield.

A catalyst from the group of the aliphatic carboxylic acids or their anhydrides, aromatic sulfonic acids, alkali metal alcoholates and alkanolamines is preferred. The preferred aliphatic carboxylic acids or anhydrides are those having 2 to 4 carbon atoms. Preferably, acetic anhydride is employed. p-Toluenesulfonic acid and phenolsulfonic acid are cited as examples of aromatic sulfonic acids. Other $C_6$-$C_{12}$ aromatic sulfonic acids can also be employed.

The alcoholate moiety in the alkali alcoholates is preferably one of 1 to 4 carbon atoms, the alcohol preferably being an alkanol; the alkanolamines are preferably also alkanolamines of 2 to 4 carbon atoms, such as triethanolamine, ethanolamine, triisopropanolamine, and 2-amino-1-butanol. The alkanolamines and alkali metal alcoholates act in amounts of as little as 0.005 moles per mole of compound of active methylene group, while the other catalysts are used in amounts of 0.03 mole and up, per mole of such compound. The maximum is 0.5 mole, but in principle one can use large amounts. Preferably, one part of the catalyst (upto 50% of its total weight) is added before starting the reaction, the other part is added during the reaction, continuously or in several portions.

The use of additional catalysts other than those named, for example, Lewis acids, pursuant to the method of U.S. Pat. No. 4,058,553, is unnecessary.

The malonic acid derivatives which can be used as reactants include, of course, the compounds containing reactive methylene groups disclosed in the above-cited U.S. Pat. No. 2,824,121. These compounds include malonic acid dinitrile, cyanoacetic acid, acetyl acetone and acetoacetic esters particularly the methyl and ethyl ester. Thus, particularly contemplated compounds for reaction with the orthoformic acid trialkyl ester include compounds having the following structural formulae.

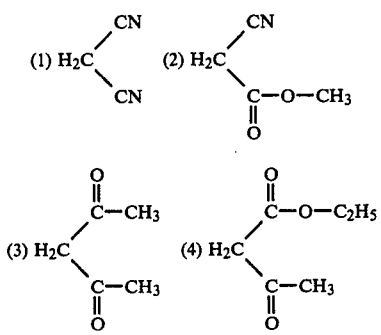

In each of the formulae (2) to (4) the $CH_3$-moiety can be replaced by a $C_2H_5$-moiety.

Where the reactant possessing the reactive methylene group has an ester function the ester function is preferably derived from a $C_1$ to $C_3$ alcohol. Preferably, the ester group is a $C_1$ to $C_3$ alkyl group. Generally speaking, the ester component will be the same ester group of the orthoformic acid trialkyl ester which can be $C_1$ to $C_4$ carbon atoms although methyl and ethyl are preferred. The molar ratio of the reactant possessing the reactive methylene group to orthoformic acid ester is, broadly speaking, 1:1.6-6.

The reaction temperature is between 90° and 165° C. It is selected such that the alcohol that forms can be distilled out. At temperatures above 160° C., excessive amounts of undesired compounds form, some of them solids, which greatly decrease the yield. At lower temperatures the transformation is poor, or products from which reduce the yield and make it very difficult or impossible to isolate economically the pure alkoxymethylene malonic acid derivatives.

The method can be practiced in a reaction flask which is equipped with a mechanical stirrer, a temperature measuring means for the reaction solution, a dropping funnel, and a fractionation column with condenser, return, and a flask for collecting the alcohol. The process can be conducted batchwise or continuously.

The method is practiced as a rule by heating to ebullition, with stirring, the mixture of malonic acid nitrile, orthoformic acid ester and catalyst in the above-given molar ratio. The alcohol that forms is continuously distilled out of the reaction mixture through a column. The heating of the solution is so regulated that the temperature of the reaction solution is between 90° and 165° C., and, when orthoformic acid triethyl ester is used, is between 60° and 80° C. at the top of the condenser. When orthoformic acid trimethylester is used, the temperature at the top of the condenser in between 55° and 70° C.

The process can be conducted at reduced pressure down to 20 mm Hg and at elevated pressure up to 5 atm. Preferably, the process is conducted at atmospheric pressure.

After the reaction has ended, the unreacted orthoformic acid ester is removed by distillation at reduced pressure and is recycled to the next batch. The alkoxymethylene compound remaining in the sump is evaporated from the residue at 0.01 to 0.2 Torr. After this single distillation it already has a purity which makes it usable in most areas of application.

The products prepared by the present method are intermediates in the preparation of pharmaceutically effective pyrimidine derivatives, such as allopurinol, for example. Products of the invention can be converted to a pharmaceutically effective pyrimidine derivative, such as allopurinol in accordance with the procedure described in German Patent Specification No. 17 70 099.

It can also be used for other condensation reactions in which the alkoxy- (or carbalkoxy)-groups and nitrile groups of the products obtained by the claimed reaction, are reacted with amidines or area compounds or amines.

In order to more fully illustrate the nature of the invention and the manner of practicing the same, the following examples are presented.

EXAMPLES

EXAMPLE 1

A two-liter, four necked flask is charged with 1332 g (9 moles) of orthoformic acid triethyl ester, 198 g (3 moles) of malonic acid dinitrile and 4 g of acetic acid anhydride. With vigorous stirring, the solution is heated to ebullition. At about 110° C. sump temperature, alcohol begins to distil out through the top of the column. During the course of the reaction, approximately 8 g of acetic acid anhydride is fed in continuously, and the heating of the reaction mixture and the reflux flow are so regulated that the temperature at the top of the condenser is between 75° and 79° C. The condensed distillate is collected and consists substantially of ethanol, acetic acid ethyl ester, formic acid ethyl ester and a small amount of orthoformic acid triethyl ester. During the reaction the sump temperature rises slowly to 130 to 140 degrees C. After 2 to 3 hours the reaction has ended. The unreacted orthoformic acid triethyl ester is distilled out through the column and is fed back to the next batch. Then ethoxymethylene malonic acid dinitrile is separated from the remainder through a simple distillation bridge at 0.1 to 0.02 Torr. In this manner, 361 g of ethoxymethylene malonic acid dinitrile is obtained, with a melting point of 64° C. and a purity of better than 99%. This corresponds to a yield of 98.7% with respect to the malonic acid dinitrile charged.

EXAMPLE 2

284 g (2.5 moles) of cyanoacetic acid ethyl ester, 740 g of orthoformic acid triethyl ester and 10 g of acetic acid anhydride are heated in the flask to ebullition with vigorous stirring. In the course of the reaction approximately 20 g of additional acetic acid anhydride is introduced. The ethanol that forms during the reaction is distilled out through the top of the column, the sump temperature rising from 130° C. to 150° C.

After about 4 hours the reaction has ended. The unreacted orthoformic acid triethyl ester is distilled out through the top of the column at reduced pressure and recycled to the next batch. Then ethoxymethylene cyanoacetic acid ethyl ester is separated from the residue through a simple distillation bridge at 0.1 to 0.2 Torr. The yield, with respect to cyanoacetic acid ethyl ester, amounts to 93% of the theory.

EXAMPLE 3

284 g (2.5 moles) of cyanoacetic acid ethyl ester, 1110 g (7.5 moles) of orthoformic acid triethyl ester and 10 g of acetic acid anhydride are brought to ebullition in a flask with vigorous stirring. During the reaction, approximately 20 g of additional acetic acid anhydride is fed in, and the ethanol that forms is removed by distillation. The reaction ends in 3½ hours. The unreacted orthoformic acid triethyl ester is distilled out through the top of the column at reduced pressure (5 to 15 Torr). In the fine vacuum, 397 g of ethoxymethylene cyanoacetic acid ethyl ester is distilled out through a distillation bridge at about 0.3 Torr. This corresponds to a yield of 94% of the theory, with respect to cyanoacetic acid ethyl ester.

EXAMPLE 4

284 g (2.5 moles) of cyanoacetic acid ethyl ester, 1110 g (7.5 moles) of orthoformic acid triethyl ester and 8 g of acetic acid anhydride are heated at ebullition in a flask with vigorous stirring. During the reaction, 23 g of additional acetic acid is fed in, and the ethanol that forms is distilled out. After 3 to 4 hours the reaction has ended.

The unreacted orthoformic acid triethyl ester is removed by distillation through the top of the column at reduced pressure (5 to 15 Torr) and recycled to the next batch. Then, 390 g of ethoxymethylene cyanoacetic acid ethyl ester is evaporated from the residue at 0.05 to 0.2 Torr through a simple distillation bridge. The yield is 92% of the theory with respect to cyanoacetic acid ethyl ester. Melting point, 53° C.

EXAMPLE 5

284 g of cyanoacetic acid ethyl ester (2.5 moles), 740 g of orthoformic acid triethyl ester (5 moles) and 10 g of propionic acid are brought to ebullition in a flask with vigorous stirring. During the reaction 25 g of additional propionic acid is fed in and the ethanol that forms is distilled out. After about 3 hours the reaction has ended.

The unreacted orthoformic acid triethyl ester is distilled out at reduced pressure (2 to 15 Torr) through the top of the column, and is recycled to the next batch. Then 380 g of ethoxymethylene cyanoacetic acid ethyl ester is evaporated from the remainder at 0.05 to 0.2 Torr through a simple distillation bridge. The yield is 90% of the theory with respect to cyanoacetic acid ethyl ester. Melting point 51° C.

EXAMPLE 6

284 g (2.5 moles) of cyanoacetic acid ethyl ester, 1100 g (7.5 moles) of orthoformic acid triethyl ester and 10 g of p-toluenesulfonic acid are heated at ebullition in a flask with vigorous stirring. During the reaction, 25 g of additional acid is fed in in portions, and the ethanol that forms in the reaction is removed by distillation. After about 4 hours the reaction has ended.

The unreacted orthoformic acid triethyl ester is distilled off through a column at reduced pressure. In the fine vacuum, 360 g of ethoxymethylene cyanoacetic acid ethyl ester is distilled out at about 0.2 Torr through a distillation bridge. This corresponds to a yield of 85% of the theory with respect to cyanoacetic acid ethyl ester. Melting point 50° to 51° C.

EXAMPLE 7

284 g (2.5 moles) of cyanoacetic acid ethyl ester, 740 g (5 moles) of orthoformic acid triethyl ester and 0.5 g of sodium methylate are brought to ebullition in a flask with vigorous stirring. The alcohol that forms in the reaction is distilled out through a column. 3½ hours later the reaction has ended. The product is worked up as described in Example 1. The yield is 88% of the theory with respect to cyanoacetic acid ethyl ester. Melting point 50° to 51° C.

EXAMPLE 8

284 g (2.5 moles) of cyanoacetic acid ethyl ester, 740 g (5 moles) of orthoformic acid triethyl ester and 5 g of triethanolamine are heated at ebullition in a flask with vigorous stirring. The alcohol that forms in the reaction is distilled out through a column. After 4 hours the reaction has ended. The product is worked up as described in Example 1. The yield is 80% of the theory with respect to cyanoacetic acid ethyl ester. Melting point 50° C.

EXAMPLE 9

284 g (2.5 moles) of cyanoacetic acid methyl ester, 530 g (5 moles) of orthoformic acid trimethyl ester and 6 g of acetic acid anhydride are heated at ebullition in a flask with vigorous stirring. During the reaction, 25 g of additional acetic acid anhydride is charged and the methanol that forms is distilled out. After 3 hours the reaction has ended.

The unreacted orthoformic acid trimethyl ester is distilled out through the top of a column and recycled to the next batch. Then 332 g of methoxymethylene cyanoacetic acid is distilled out through a simple distillation bridge. The yield amounts to 94% of the theory with respect to cyanoacetic acid methyl ester. Melting point 97° C.

EXAMPLE 10

Ethoxymethylene acetylacetone 253 g (2.5 moles) of acetylacetone, 1,110 g (7.5 moles) of orthformic acid triethyl ester and 8 g of acetic anhydride are heated to ebullition in a flask with vigorous stirring. During the reaction, about 23 g of acetic acid is added and the ethanol formed is distilled off. After 2 to 3 hours the reaction is completed. The unreacted orthoformic acid triethyl ester is distilled out at reduced pressure (5 to 1 Torr) through the top of the column and fed back to the next batch. Following this, 355 g of ethoxymethylene acetylacetone is evaporated, separated from the residue through a simple distillation bridge at 0.1 to 0.3 Torr. The yield, referred to acetylacetone, was 91% of theory.

EXAMPLE 11

Ethoxymethylene acetoacetic acid ethyl ester

A two-liter four-neck flask provided with stirrer, column and dropping funnel is charged with 1132 g (9 moles) of orthoformic acid triethyl ester, 390 g (3 moles) of acetoacetic acid ethyl ester and 18 g of acetic anhydride. The solution is heated to ebullition with vigorous stirring. At 130° C. sump temperature, alcohol begins to distill out through the top of the column. During the course of the reaction approximately 32 g of acetic anhydride is added dropwise. The heating of the reaction solution and the reflux flow are regulated so that the temperatures at the top of the column are between 70° to 79° C. The condensed distillate is collected and consists substantially of ethanol, acetic acid ethyl ester, formic acid ethyl ester and a small amount of orthoformic acid triethyl ester. During the reaction the sump temperature rises slowly to 130° to 140° C. The reaction is completed after 2 to 3 hours. The unreacted orthoformic acid triethyl ester is distilled out through the column at 2 to 20 Torr and is fed back to the next batch. Ethoxymethylene acetoacetic ester is then evaporated/separated from the residue at 0.1 Torr through a simple distillation bridge. In this manner, 520 g of ethoxymethylene acetoacetic ester of a purity of <99% is obtained. This corresponds to a yield of ~93%, referred to the acetoacetic acid ethyl ester charged.

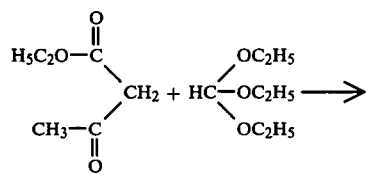

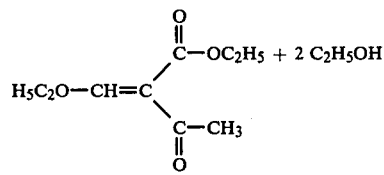

COMPARATIVE EXAMPLE 66 g (1 mol) malonic dinitrile, 220 g (1.5 mol) orthoformic acid tri-ethylester and 6 g acetic acid anhydride are heated, while stirring vigorously, to ebullition in a flask. During the reaction, approximately 6 g acetic acid anhydride is added continuously. The alcohol and the formic acid ester developing during the reaction are distilled out through the top of the column, while the sump temperature rises from 130° C. to 150° C.

After approximately 2 hours, the reaction is completed. At reduced pressure, the unreacted orthoformic triethyl ester is distilled off through the top of the column. Subsequently, 108 g ethoxymethylene malonic dinitrile, i.e., 98.5% of theory with respect to malonic dinitrile, with a content of 97% is evaporated from the remainder. After the recrystallization from ethanol, the product obtained had a purity of 99.3% according to GC analysis.

What is claimed is:

1. In a process for the preparation of an alkoxymethylene malonic acid derivative which comprises contacting a compound selected from the group consisting of

 (1)

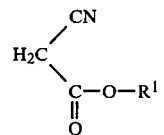 (2)

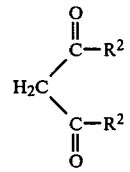 (3)

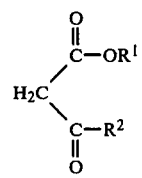 (4)

wherein $R^1$ is $C_1$ to $C_3$ alkyl, and $R^2$ is methyl or ethyl with an orthoformic acid trialkyl ester in the presence of a catalyst at a temperature of 80° to 165° C., the improvement residing in employing at least 1.6 mols of orthoformic acid ester per mol of said compound and carrying out the process in the presence of a catalyst consisting essentially of an aliphatic carboxylic acid of 2 to 4 carbon atoms and in the absence of a Lewis acid catalyst other than the aliphatic carboxylic acid of 2 to 4 carbon atoms, said carboxylic acid in an amount of up to 50% of the total amount of carboxylic acid to be employed being added to the reaction mixture before commencement of the reaction and the balance of the carboxylic acid being added during the reaction continuously or in several portions, the alcohol being formed being removed during the process.

2. In a process for the preparation of an alkoxymethylene malonic acid derivative by reaction of a compound selected from the group consisting of

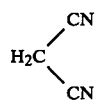 (1)

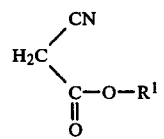 (2)

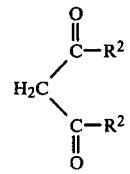 (3)

-continued

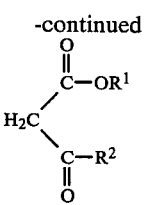
(4)

wherein R¹ is C₁ to C₃ alkyl, and R² is methyl or ethyl with an orthoformic acid trialkyl ester having 1 to 3 carbon atoms in the alkyl group in the presence of a catalyst, the improvement which comprises employing 1.6 to 6 mols of orthoformic acid ester per mol of said compound and performing the process at a temperature between 80° and 165° C. in the presence of an effective amount of up to 0.5 mol per mol of said compound of a catalyst consisting essentially of an aliphatic carboxylic acid of 2 to 4 carbon atoms and in the absence of a Lewis acid catalyst other than the aliphatic carboxylic acid of 2 to 4 carbon atoms, a portion of said carboxylic acid in an amount of up to 50% of the total amount of carboxylic acid to be employed being introduced to the reaction mixture before commencement of the reaction and the balance of the carboxylic acid being added to the reaction mixture during the reaction continuously or in several portions, the alcohol being formed being removed during the process.

3. In a process for the preparation of an alkoxymethylene malonic acid derivative which comprises contacting a compound from the group consisting of

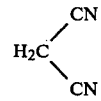
(1)

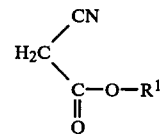
(2)

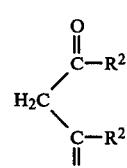
(3)

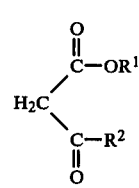
(4)

wherein R¹ is C₁ to C₃ alkyl, and R² is methyl or ethyl with an orthoformic acid trialkyl ester in the presence of a catalyst at a temperature of 80° to 165° C., the improvement residing in employing at least 1.6 mols of orthoformic acid ester per mol of said compound and carrying out the process in the presence of a catalyst consisting essentially of an aliphatic carboxylic acid of 2 to 4 carbon atoms and in the absence of any acid, other than the aliphatic carboxylic acid of 2 to 4 carbon atoms, which is an electron exceptor, said carboxylic acid in an amount of up to 50% of the total amount of carboxylic acid to be employed being added to the reaction mixture before commencement of the reaction, the balance of the carboxylic acid being added to the reaction continuously or in several portions, the alcohol being formed being removed during the process.

4. In a process for the preparation of an alkoxymethylene malonic acid derivative by reaction of a compound selected from the group consisting of

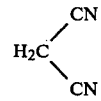
(1)

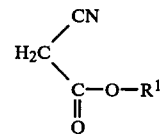
(2)

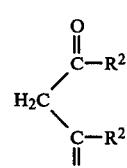
(3)

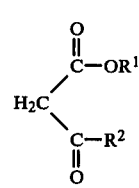
(4)

wherein R¹ is C₁ to C₃ alkyl, and R² is methyl or ethyl with an orthoformic acid trialkyl ester having 1 to 3 carbon atoms in the alkyl group in the presence of a catalyst, the improvement which comprises employing 1.6 to 6 mols of orthoformic acid ester per mol of said compound and performing the process at a temperature between 80° and 165° C. in the presence of an effective amount of up to 0.5 mol per mol of said compound of a catalyst consisting essentially of an aliphatic carboxylic acid of 2 to 4 carbon atoms and in the absence of any acid, other than the aliphatic carboxylic acid of 2 to 4 carbon atoms, which is an electron exceptor, a portion of said carboxylic acid in an amount of up to 50% of the total amount of carboxylic acid to be employed being introduced to the reaction mixture before commencement of the reaction and the balance of the carboxylic acid being added to the reaction mixture during the reaction continuously or in several portions, the alcohol being formed being removed during the process.

5. A process according to claim 1, wherein said compound is

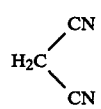
(1)

6. A process according to claim 1, wherein said compound is

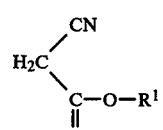
(2)

* * * * *

UNITED STATES PATENT AND TRADEMARK OFFICE
CERTIFICATE OF CORRECTION

PATENT NO. : 4,468,353

DATED : August 28, 1984

INVENTOR(S) : Otto Ackermann, et al

It is certified that error appears in the above-identified patent and that said Letters Patent is hereby corrected as shown below:

Col. 7, line 55          Delete "98.5" and insert --88.5--

Signed and Sealed this

Twenty-fourth Day of September 1985

[SEAL]

Attest:

DONALD J. QUIGG

Attesting Officer

Commissioner of Patents and
Trademarks—Designate